United States Patent
Kuriyama

(10) Patent No.: US 11,196,926 B2
(45) Date of Patent: Dec. 7, 2021

(54) BLUR CORRECTION DEVICE, ENDOSCOPE APPARATUS, AND BLUR CORRECTION METHOD

(71) Applicant: OLYMPUS CORPORATION, Tokyo (JP)

(72) Inventor: Naoya Kuriyama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 263 days.

(21) Appl. No.: 16/683,721

(22) Filed: Nov. 14, 2019

(65) Prior Publication Data
US 2020/0084380 A1    Mar. 12, 2020

Related U.S. Application Data

(63) Continuation of application No. PCT/JP2017/018906, filed on May 19, 2017.

(51) Int. Cl.
*G06T 7/10* (2017.01)
*H04N 5/232* (2006.01)
(Continued)

(52) U.S. Cl.
CPC ..... *H04N 5/23267* (2013.01); *A61B 1/00009* (2013.01); *A61B 1/00089* (2013.01); *A61B 1/00188* (2013.01); *A61B 1/042* (2013.01); *A61B 1/045* (2013.01); *A61B 17/00234* (2013.01); *G06T 3/4023* (2013.01); *G06T 5/003* (2013.01); *G06T 7/10* (2017.01); *G06T 7/11* (2017.01); *G06T 7/20* (2013.01); *G06T 7/90* (2017.01); *H04N 5/2251* (2013.01); *A61B 1/07* (2013.01); *A61B 2017/00269* (2013.01);
(Continued)

(58) Field of Classification Search
CPC ....... H04N 5/23267; H04N 2005/2255; H04N 5/23254; H04N 5/2251; G06T 7/10; G06T 7/11; G06T 7/90; G06T 3/4023; G06T 5/003; G06T 7/20; G06T 2207/10068; G06T 2207/20201; A61B 1/042; A61B 1/00188; A61B 1/00009; A61B 1/00089; A61B 1/045; A61B 17/00234; A61B 1/07; A61B 2017/00269; G02B 23/24; G03B 5/00
USPC ...................................................... 382/275
See application file for complete search history.

(56) References Cited

U.S. PATENT DOCUMENTS

2019/0268538 A1*    8/2019    Shiratani ............ A61B 1/00009

FOREIGN PATENT DOCUMENTS

| JP | 2009-088628 A | 4/2009 |
| JP | 2015-096237 A | 5/2015 |
| WO | WO 2016/088628 A1 | 6/2016 |

OTHER PUBLICATIONS

International Search Report dated Jul. 18, 2017 issued in PCT/JP2017/018906.

* cited by examiner

*Primary Examiner* — Amandeep Saini
(74) *Attorney, Agent, or Firm* — Scully, Scott, Murphy & Presser, P.C.

(57) ABSTRACT

A blur correction device includes a processor including hardware, and the processor obtains an object image from an imaging section, sets any one of a first region where a blur correction is not applied and a second region where the blur correction is applied, based on the object image, finds a third region representing a result of the blur correction applied to the second region, and combines the third region and the first region.

19 Claims, 12 Drawing Sheets

(51) Int. Cl.
*G06T 7/90* (2017.01)
*A61B 1/00* (2006.01)
*A61B 1/045* (2006.01)
*A61B 17/00* (2006.01)
*G06T 3/40* (2006.01)
*G06T 5/00* (2006.01)
*G06T 7/20* (2017.01)
*H04N 5/225* (2006.01)
*A61B 1/04* (2006.01)
*G06T 7/11* (2017.01)
*A61B 1/07* (2006.01)

(52) U.S. Cl.
CPC ............... *G06T 2207/10068* (2013.01); *G06T 2207/20201* (2013.01); *H04N 2005/2255* (2013.01)

BLUR CORRECTION DEVICE, ENDOSCOPE APPARATUS, AND BLUR CORRECTION METHOD

CROSS REFERENCE TO RELATED APPLICATION

This application is a continuation of International Patent Application No. PCT/JP2017/018906, having an international filing date of May 19, 2017, which designated the United States, the entirety of which is incorporated herein by reference.

BACKGROUND

An endoscopic examination is usually performed by repeating a process including roughly determining an observation target by screening and then closely observing the observation target to diagnose. In the close observation, a relatively inexperienced user may cause a shake, which destabilizes a field of vision and thus extends examination time.

In order to solve such a problem, JP-A-2009-88628 discloses a method for stabilizing the field of vision by detecting a motion of an object and eliminating a component resulted from the shake from motion components so as to trim an image (perform a blur correction).

In the endoscopic examination, a member called as a hood may be attached to a distal end of an endoscope in order to turn up a wall of a large intestine or the like.

SUMMARY

In accordance with one of some embodiments, there is provided a blur correction device comprising a processor including hardware, the processor being configured to implement:

obtaining an object image from an imaging section that forms an image of reflected light from an object;

setting any one of a first region where a blur correction is not applied and a second region where the blur correction is applied, based on the object image;

finding a third region representing a result of the blur correction applied to the second region; and combining the third region and the first region.

In accordance with one of some embodiments, there is provided an endoscope apparatus comprising:

the blur correction device;

an insertion section configured to be inserted into a body;

a hood configured to be attached to a distal end of the insertion section; and an image sensor configured to be connected to the insertion section.

In accordance with one of some embodiments, there is provided a blur correction method comprising:

obtaining an object image from an imaging section that forms an image of reflected light from an object;

setting any one of a first region where a blur correction is not applied and a second region where the blur correction is applied, based on the object image;

finding a third region representing a result of the blur correction applied to the second region; and combining the third region and the first region.

In accordance with one of some embodiments, there is provided a blur correction device comprising:

an image acquisition section configured to obtain an object image from an imaging section configured to form an image of reflected light from an object;

a region detection section configured to detect a first region where a blur correction is not applied based on the object image; and a blur correction processing section configured to find a third region representing a result of the blur correction applied to a second region, and to combine the third region and the first region, the second region being a region excluding the first region from the object image.

DESCRIPTION OF EXEMPLARY EMBODIMENTS

Figure 1:
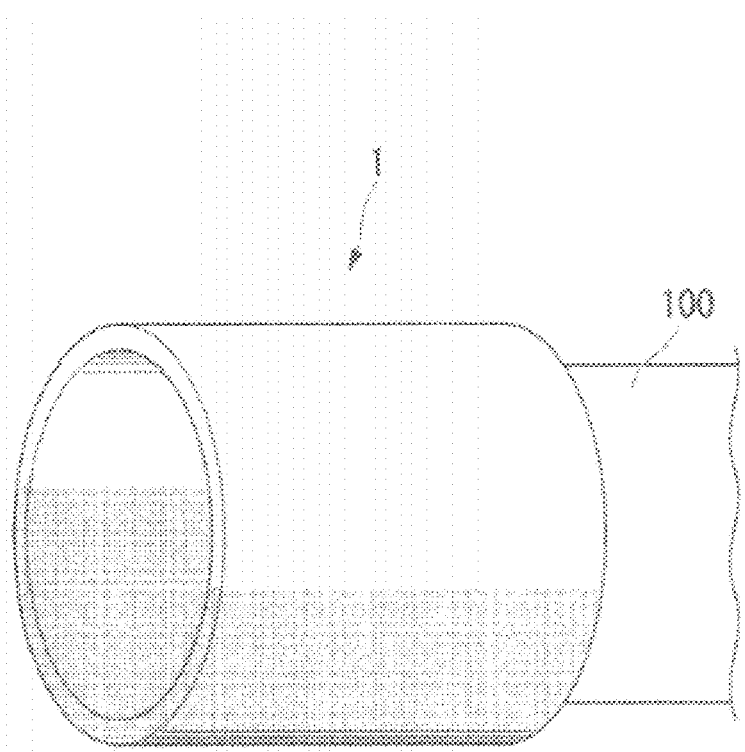
FIG. 1 is an example of attachment of a hood to an endoscope apparatus.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Exemplary embodiments are described below. Note that the following exemplary embodiments do not in any way limit the scope of the content defined by the claims laid out herein. Note also that all of the elements described in the present embodiment should not necessarily be taken as essential elements.

1. Method According to Present Embodiment

First of all, a method according to the present embodiment is described. The method according to the present embodiment is described hereinafter by taking an endoscope apparatus for an example. However, since the method is effective when a member fixed to an imaging section appears in an object image, the method can be applied to a device (blur correction device or imaging device) other than the endoscope apparatus.

As illustrated in FIG. 1, when a treatment is performed using a treatment tool while tissue is observed with the endoscope apparatus, a hood 1 may be attached to a distal end of an insertion section 100 (endoscopic scope) of the endoscope apparatus to secure a field of vision of the endoscope apparatus and a space to perform the treatment.

Figure 2:
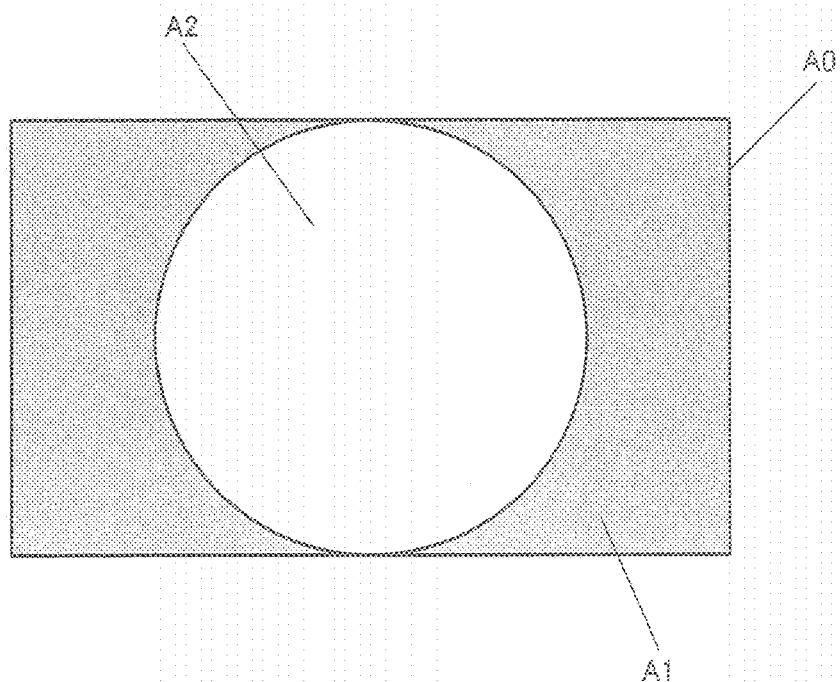
FIG. 2 is an example of an object image with the hood attached.

FIG. 2 illustrates an example of an object image imaged by an imaging section 200 of the endoscope apparatus with the hood 1 attached. As illustrated in FIG. 2, an object image (A0) includes a region (A1) where the hood 1 appears and a region (A2) excluding the region A1 serving as an observation field of vision where a desired object such as the tissue is imaged.

As a treatment to excise biological tissue such as mucosa using the endoscope apparatus, endoscopic submucosal dissection (ESD) is known. In the ESD, in order to excise a lesion part on a surface of a digestive tract, normal mucosa outside the lesion part is dissected over an entire circumference, submucosa is then exfoliated, and the lesion part is excised. In the ESD, the distal end of the endoscope apparatus with the hood 1 attached is inserted between the dissected submucosa and a muscle layer, and the submucosa is continuously dissected with a high frequency knife in this state so as to eventually exfoliate the lesion part.

Figure 3:
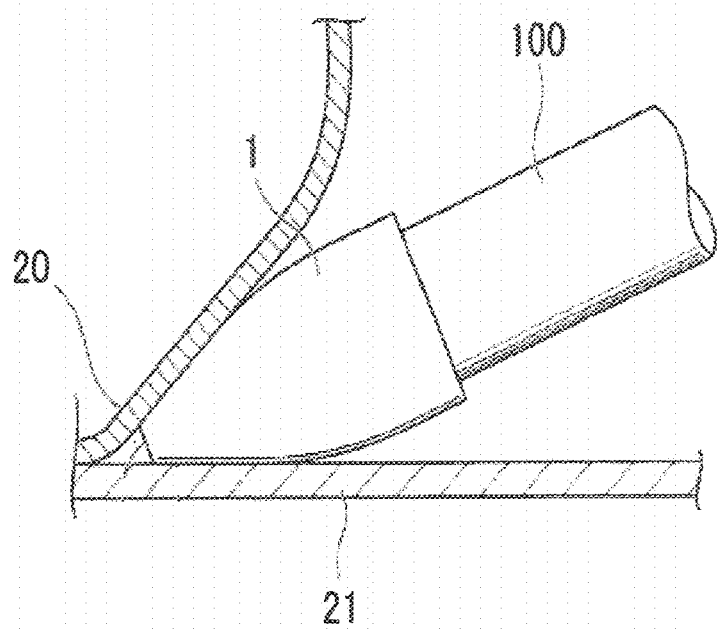
FIG. 3 is a diagram illustrating a situation where the hood is in contact with tissue.

FIG. 3 is a diagram illustrating elastic deformation of the hood 1 in the ESD. As illustrated in FIG. 3, when a user (physician or operating surgeon) inserts the hood 1 between submucosa 20 and a muscle layer 21, the hood 1 receives pressing force and is elastically deformed. In this case, a shape of a region where the hood 1 appears in the object image changes. That is, when the shape of the region where the hood 1 appears changes, the user operating the endoscope apparatus may presume that the hood 1 is in contact with the tissue.

In addition, there is a well-known method for performing an electronic blur correction on the object image. When a shake of an imaging section (i.e., a relative motion between an object and the imaging section in a broad sense) occurs, the object moves in the image. However, performing the electronic blur correction can reduce the motion of the object in the image. In a magnifying observation of the object, an impact of the shake is larger (i.e., a motion of the object in the image is larger) than that in an unmagnifying observation. Thus, the blur correction becomes more important. With the endoscope apparatus, the magnifying observation is performed in the treatment such as the ESD. Therefore, the blur correction is highly likely to be performed with the hood 1 attached.

Figure 4:
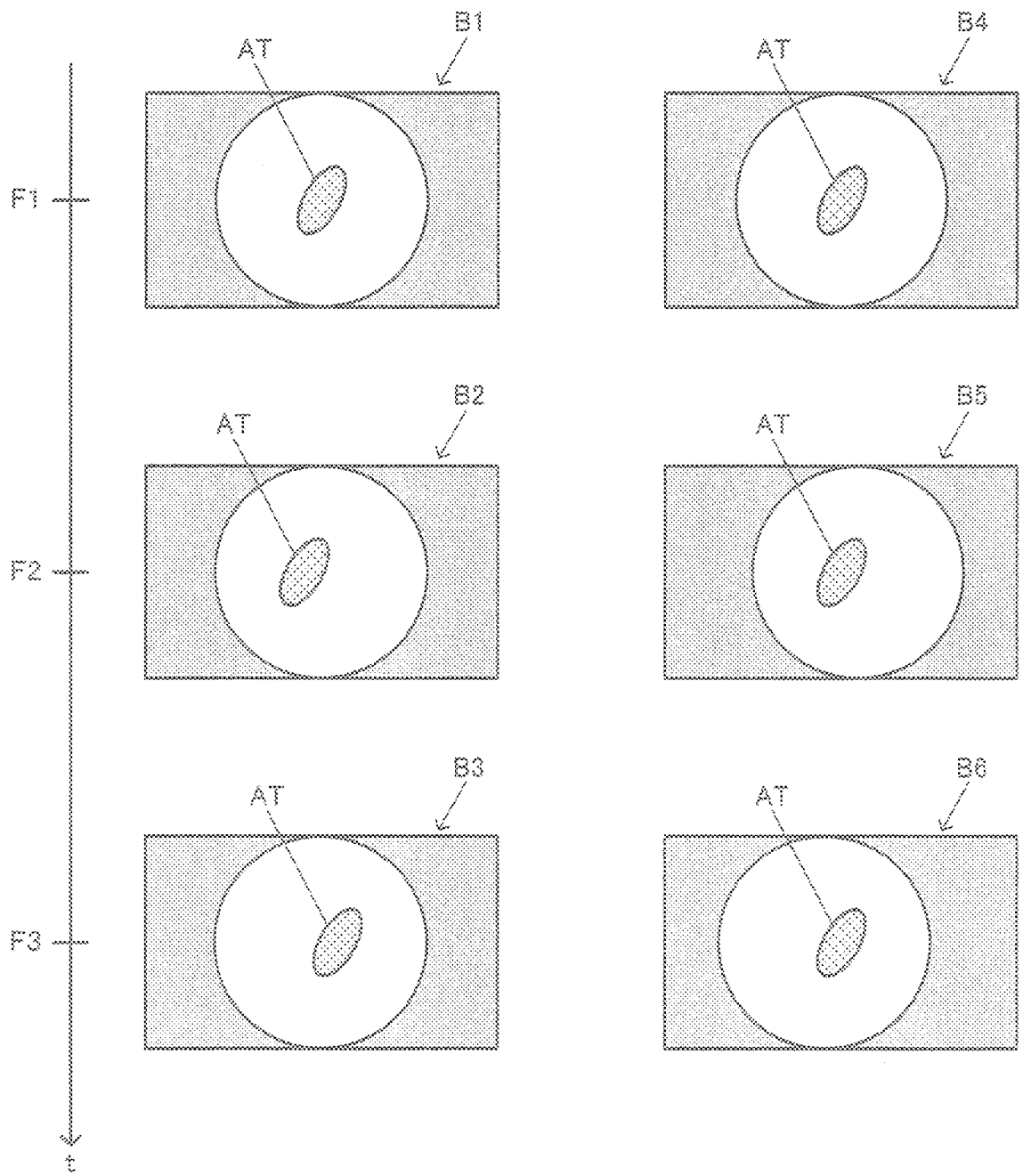
FIG. 4 is a comparative example illustrating a conventional blur correction.

FIG. 4 is a diagram illustrating a comparative example to the present embodiment, and illustrating changes in object images when a known electronic blur correction is performed with the hood 1 attached. In FIG. 4, a vertical direction represents a change in time, and images B1 to B3 represent the object images before the blur correction is applied. Note that in FIG. 4, in order to clearly indicate the change in the image by the blur correction, description is given assuming that an object AT serving as an observation target is imaged in a center of the image B1.

In examples in the images B1 to B3 in FIG. 4, assuming that the object image in a given frame F1 is a reference, the object AT serving as the observation target moves in a left direction in the image in a next frame F2, and the object AT moves in a right direction in the image in a frame F3 after next. The hood 1 is attached to the imaging section 200 (insertion section 100) as illustrated in FIG. 1. Except for a state where the hood 1 is in contact with the tissue as illustrated in FIG. 3, a position of the region where the hood 1 appears in the object image does not change as illustrated in the images B1 to B3.

Images B4 to B6 in FIG. 4 represent examples of output images (display images) when a conventional blur correction is performed on the object images B1 to B3. The blur correction cancels the motion of the object. Accordingly, the image B5 is an image obtained when the object image B2 is moved in a right direction, and the image B6 is an image obtained when the object image B3 is moved in a left direction. As illustrated in the images B4 to B6, performing the blur correction can prevent a change in position of the object (e.g., the tissue) in the captured image through a plurality of frames F1 to F3. In the examples shown by the images B4 to B6 in FIG. 4, the position of the object AT serving as the observation target can be fixed in the center of each object image, thereby facilitating the observation and the treatment by the user.

However, a general blur correction takes an entire object image as a target. Accordingly, the region where the hood 1 appears also changes in the image after the blur correction. The region where the hood 1 appears moves in the right direction in the image B5 and in the left direction in the image B6.

As described above, in the case where the blur correction is not performed, the region where the hood 1 appears in the object image is fixed when the hood 1 and the tissue is in a non-contact state, and changes when the hood 1 comes into contact with the tissue. That is, performing the blur correction illustrated in FIG. 4 may cause the user to misunderstand the motion of the region where the hood 1 appears in the image due to the blur correction as the motion due to the contact with the tissue.

As described above, in spite of high importance of the blur correction with the hood 1 attached, performing the conventional blur correction may only mislead the user and disturb the observation and the treatment.

Thus, according to the present embodiment, a process in the blur correction is changed depending on whether the region requires the blur correction. A blur correction device according to the present embodiment includes a processor including hardware. The processor obtains the object image from the imaging section 200 that forms the image of reflected light from the object, and sets any one of a first region where the blur correction is not applied and a second region where the blur correction is applied, based on the object image. The processor further finds a third region representing a result of the blur correction applied to the second region, and combines the third region thus found and the first region. The first region corresponds to a blur correction non-required region in the description below. The second region corresponds to a blur correction target region. The third region corresponds to a blur-corrected region.

Alternatively, the blur correction device (endoscope apparatus) according to the present embodiment includes, as will be described later with reference to FIG. 6, an image acquisition section (corresponding to an A/D conversion section 310 in a narrow sense), a blur correction non-required region detection section 330, and a blur correction processing section 370. The image acquisition section obtains the object image from the imaging section 200 that forms the image of the reflected light from the object. The blur correction non-required region detection section 330 detects the blur correction non-required region based on the object image. The blur correction processing section 370 finds the blur-corrected region corresponding to the result of the blur correction applied to the blur correction target region assuming that a region excluding the blur correction non-required region from the object image is the blur correction target region, and combines the found blur-corrected region and the blur correction non-required region. The blur correction device according to the present embodiment corresponds to a processing section 300 of the endoscope apparatus in FIG. 6, for example.

The blur correction non-required region described herein represents a region where the blur correction is not required (i.e., a region where a motion or a change in shape due to the blur correction is not desired to occur), and corresponds to the region where the hood 1 appears in the object image, for example. A region where a member whose relative positional relationship with respect to the imaging section 200 does not change much (i.e., a member that is fixed to the imaging section 200) appears in the object image may be considered as the blur correction non-required region. The blur correction target region is a region excluding the blur correction non-required region from the object image. The blur-corrected region is a region that represents the result of the blur correction applied to the blur correction target region. The blur correction processing section 370 only needs to find the blur-corrected region, and thus a processing procedure can be implemented in various modified manners. As will be described later, the blur correction processing section 370 may find the blur-corrected region by performing the blur correction only on the blur correction target region in the object image. Or, the blur correction processing section 370 may find the blur-corrected region by performing the blur correction on the entire object image and then cancelling the blur correction in the region corresponding to the blur correction non-required region.

Figure 5:
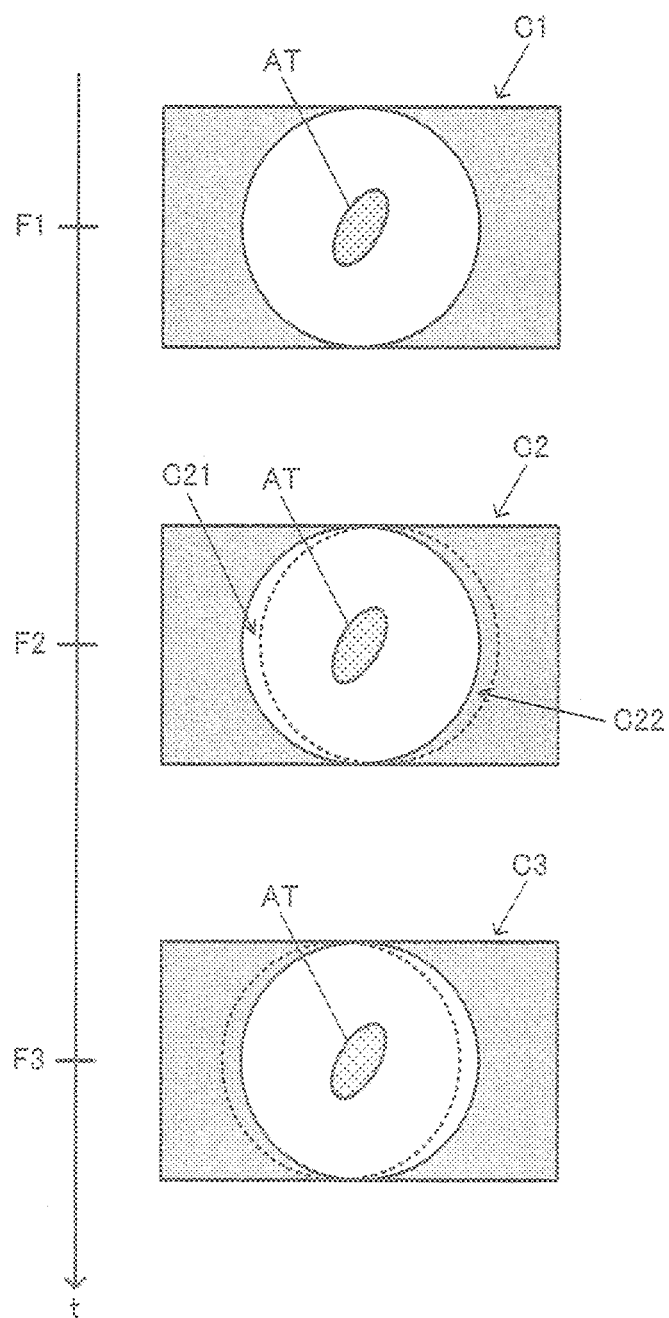
FIG. 5 is a diagram illustrating a blur correction according to the present embodiment.

Images C1 to C3 in FIG. 5 represent examples of display images when the blur correction is performed on the images B1 to B3 in FIG. 4 in the method according to the present embodiment. As illustrated in the image C2, according to the method of the present embodiment, the blur correction is not performed on the region corresponding to the hood 1, and only the region excluding the hood 1 moves in the right direction due to the blur correction. In the image C3, the blur correction is not performed on the region corresponding to the hood 1, and only the region excluding the hood 1 moves in the left direction due to the blur correction. A circular region illustrated by a dotted line in each of the images C2 and C3 represents the result of the blur correction of the region excluding the hood 1 (i.e., the blur-corrected region). As illustrated in FIG. 5, the method according to the present embodiment can reduce the blur of the object (e.g., the object AT) while preventing the blur correction non-required region from moving due to the blur correction. As for the example of the endoscope apparatus, the motion of the tissue due to the shake can be prevented while the motion of the hood 1 in the image is prevented, thereby preventing misleading the user into believing that the hood 1 comes into contact with the tissue.

Meanwhile, in the example of the image C2, moving the region excluding the hood 1 in the right direction causes a pixel value of a pixel in some part (C21) to be undefined. In addition, moving the region excluding the hood 1 in the right direction causes an overlap on a region of the hood 1, and thus two kinds of pixel values are obtained from a pixel in other part (C22). A process for these parts will be described later.

As described above, the method according to the present embodiment can be applied to the endoscope apparatus including the blur correction device (processing section 300) described above. By applying the method according to the present embodiment to the endoscope apparatus, the blur correction can be appropriately performed with the hood 1 attached.

Moreover, the method according to the present embodiment can be applied to a blur correction method including obtaining the object image from the imaging section 200 that forms the image of the reflected light from the object, detecting the blur correction non-required region based on the object image, finding the blur-corrected region corresponding to the result of the blur correction applied to the blur correction target region assuming that the region excluding the blur correction non-required region from the object image is the blur correction target region, and combining the blur-corrected region and the blur correction non-required region.

Processes of the blur correction device or the like according to the present embodiment may be partially or mainly implemented with a program. In this case, the blur correction device according to the present embodiment is implemented by a processor such as a central processing unit (CPU) executing the program. Specifically, the program stored in a non-transitory information storage device is read and executed by the processor such as the CPU. The information storage device (e.g., a computer-readable device or a medium) stores the program and data. A function of the information storage device can be implemented with an optical disk (e.g., a digital versatile disk (DVD) or a compact disk (CD)), a hard disk drive (HDD), or a memory (e.g., a card-type memory or a read only memory (ROM)). The processor such as the CPU performs various processes according to the present embodiment based on the program (data) stored in the information storage device. Thus, the information storage device stores the program causing a computer (device including an operation section, a processing section, a storage section, and an output section) to function as components according to the present embodiment (i.e., the program causing the computer to execute the processes of the components).

The blur correction device or the like according to the present embodiment may include the processor and the memory. The processor described herein may have functions of sections each implemented by individual hardware, or the functions of sections each implemented by integrated hardware, for example. For example, the processor may include hardware, and the hardware may include at least one of a circuit that processes a digital signal and a circuit that processes an analog signal. For example, the processor may include one or more circuit devices (e.g., an integrated circuit (IC)) mounted on a circuit board, or one or more circuit elements (e.g., a resistor or a capacitor). The processor may be the CPU, for example. Note that the processor is not limited to the CPU, but various other processors such as a graphics processing unit (GPU) or a digital signal processor (DSP) may also be used. The processor may be a hardware circuit that includes an application specific integrated circuit (ASIC). The processor may include an amplifier circuit, a filter circuit, and the like that process an analog signal. The memory may be a semiconductor memory such as a static random access memory (SRAM) or a dynamic random access memory (DRAM), a register, a magnetic storage device such as a hard disk drive, or an optical storage device such as an optical disc device. For example, the memory stores a computer-readable instruction, and the function of each section of the blur correction device is implemented by causing the processor to perform the instruction. The instruction described herein may be an instruction set that is included in a program, or may be an instruction that instructs the hardware circuit included in the processor to operate.

2. System Configuration Example

Figure 6:
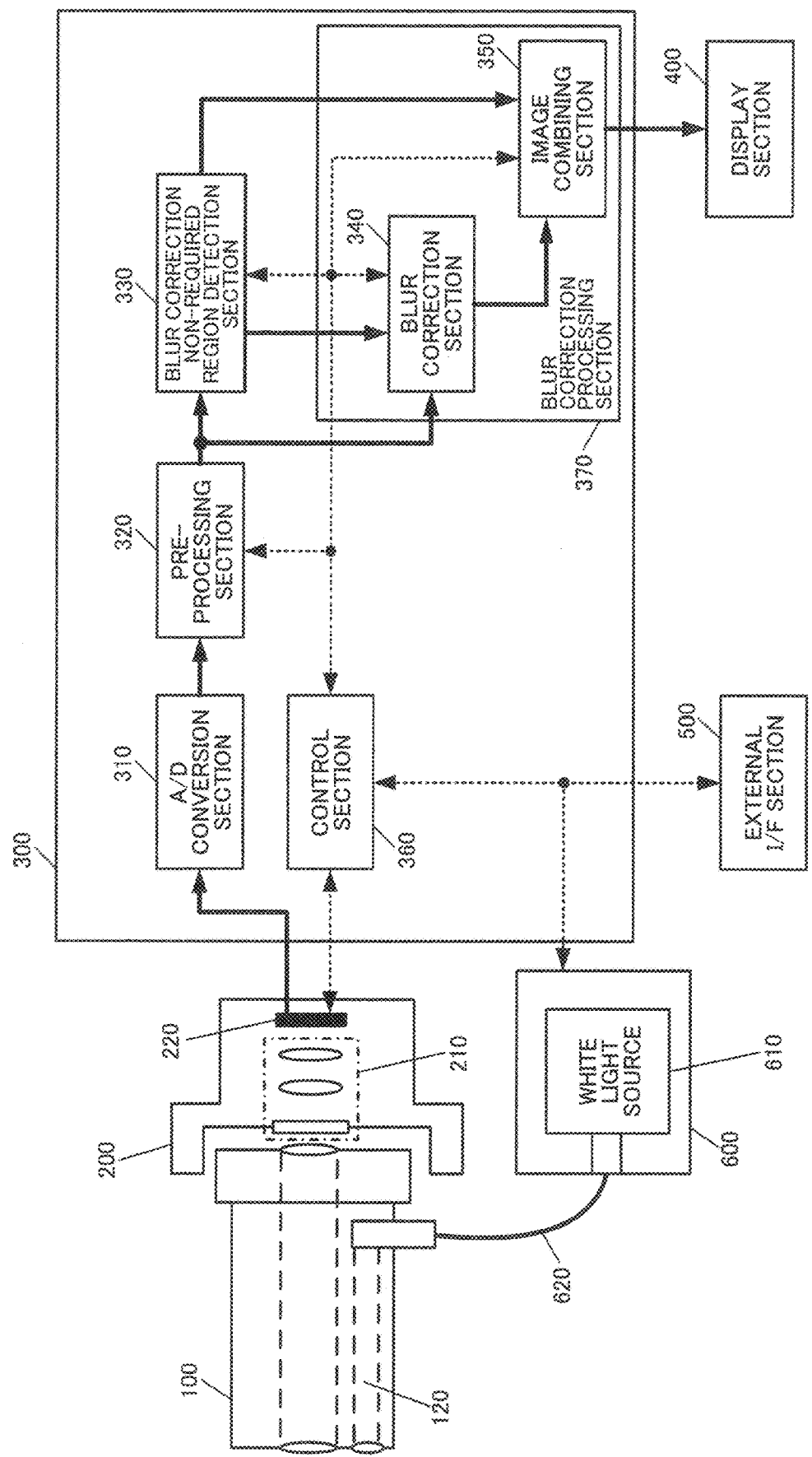
FIG. 6 is a configuration example of the endoscope apparatus according to the present embodiment.

FIG. 6 illustrates a configuration example of the endoscope apparatus (endoscope system) according to the present embodiment. The endoscope apparatus includes the insertion section 100 that is inserted into a body, the imaging section 200 connected to the insertion section 100, the processing section 300 (processing device or processing circuit), a display section 400 (display), an external I/F section 500, and a light source section 600.

The light source section 600 includes a white light source 610 that emits white light, and a light guide cable 620 that guides the light emitted from the white light source 610 to the insertion section 100. The insertion section 100 includes a member in a long and narrow tubular shape that can curve so as to be inserted into the body. A light guide section 120 of the insertion section 100 guides light emitted from the light guide cable 620 to the distal end of the endoscope.

The imaging section 200 forms an image (object image) from reflected light from the object. The imaging section 200 includes an objective lens system 210 and an image sensor 220. The objective lens system 210 forms an image from reflected light that is light emitted from the light guide section 120 and reflected on the object. The image sensor 220 photoelectrically converts the reflected light formed into the image with the objective lens system 210 into an image.

The processing section 300 performs signal processing including image processing. The processing section 300 includes an A/D conversion section 310 (image acquisition section or A/D conversion circuit), a pre-processing section 320, a blur correction non-required region detection section 330, a blur correction processing section 370, and a control section 360. The blur correction processing section 370 includes a blur correction section 340 and an image combining section 350.

The A/D conversion section 310 converts analog signals sequentially output from the image sensor 220 into digital images and sequentially outputs the digital images to the pre-processing section 320. The pre-processing section 320 performs image processing including a white balance process, an interpolation process (demosaicing process), and the like on the images output from the A/D conversion section 310, and sequentially outputs the resultant images to the blur correction non-required region detection section 330, the blur correction processing section 370 (blur correction section 340).

The blur correction non-required region detection section 330 performs a process for detecting the blur correction non-required region on the object image output from the pre-processing section 320. The process for detecting the blur correction non-required region will be described later in detail. The blur correction non-required region detection section 330 may detect the blur correction non-required region in each frame, or stop detecting after detecting once until a specific requirement is satisfied. The blur correction non-required region detection section 330 outputs information about the detected blur correction non-required region to the blur correction processing section 370 (blur correction section 340 and image combining section 350).

The blur correction processing section 370 performs the blur correction and outputs an output image (blur-corrected image or display image) to the display section 400. The blur correction section 340 finds motion information from object images in time series, and performs the blur correction based on the found motion information. At this time, the blur correction section 340 finds the blur-corrected region based on the blur correction non-required region, and outputs the found blur-corrected region to the image combining section 350. The image combining section 350 combines the blur-corrected region received from the blur correction section 340 and the blur correction non-required region received from the blur correction non-required region detection section 330 so as to form the combined image. The image combining section 350 outputs the combined image to the display section 400 as an output image.

Note that the processor may detect a fourth region that belongs to neither the third region nor the first region. The fourth region corresponds to a blank region in the description below. When the blank region exists between the blur-corrected region and the blur correction non-required region, the blur correction processing section 370 (blur correction section 340, specifically) may further process the blur-corrected region. Alternatively, the blur correction section 340 may previously process at least one of the blur correction target region and the blur correction non-required region, and then perform a blur correction process. The process performed by the blur correction processing section 370 will be described later in detail.

The control section 360 is bidirectionally connected to the external I/F section 500, the light source section 600, the image sensor 220, the pre-processing section 320, the blur correction non-required region detection section 330, the blur correction processing section 370, and the like to input and output control signals.

The display section 400 is, for example, a liquid crystal monitor, and sequentially displays the combined images output from the image combining section 350. The external I/F section 500 is an interface used for input to the endoscope apparatus by the user or the like. For example, the external I/F section 500 includes an adjustment button for adjusting a parameter for the image processing or the like.

3. Details of Blur Correction Non-Required Region Detection Section 3.1 Detection by Color of Pixel A method for detecting the blur correction non-required region from the object image is described. The hood 1 illustrated in FIG. 1 is made of a silicone rubber or the like, and a color of the hood 1 is presumed to be different from a color of the desired object (color of tissue in a case of the endoscope apparatus).

Thus, the blur correction non-required region detection section 330 detects the blur correction non-required region based on a color of a pixel in the object image. For example, the blur correction non-required region detection section 330 detects a region where the color of the pixel in the object image is achromatic as the blur correction non-required region. The hood 1 is usually achromatic such as gray or black. Therefore, the blur correction non-required region detection section 330 can appropriately detect the blur correction non-required region by detecting an achromatic region from an object region.

Figure 7:
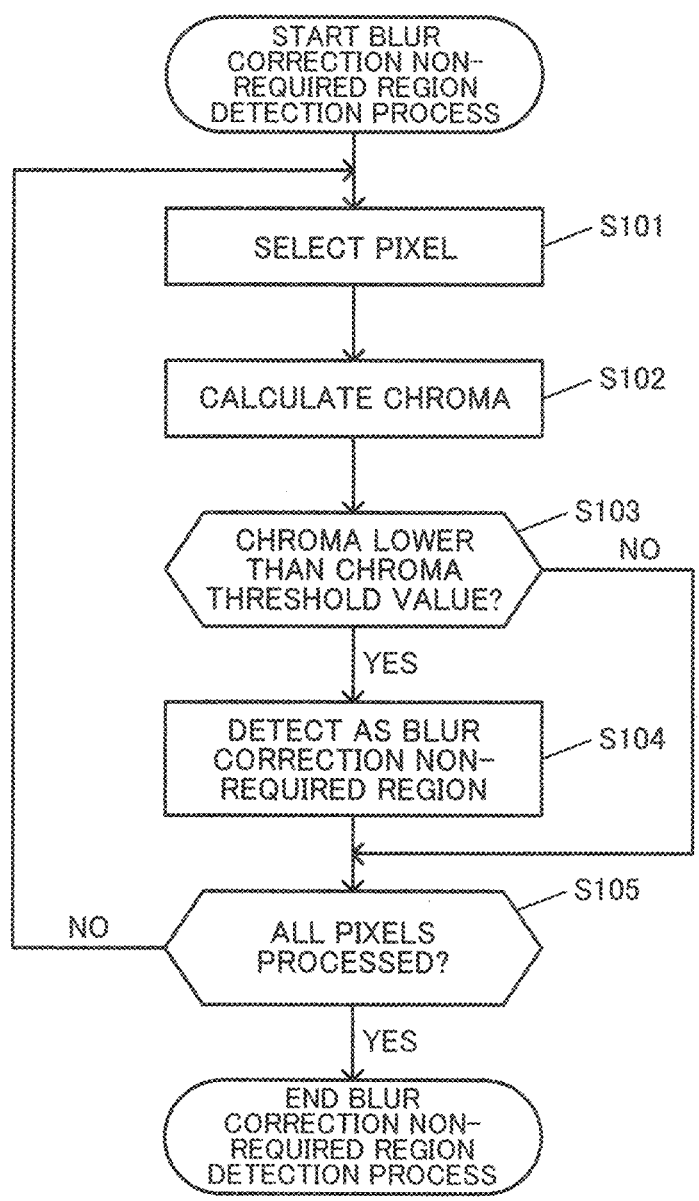
FIG. 7 is a flowchart illustrating a blur correction non-required region detection process.

FIG. 7 is a flowchart illustrating a blur correction non-required region detection process using chroma. When the process starts, the blur correction non-required region detection section 330 selects a pixel serving as a processing target from the object image (S101). Next, the blur correction non-required region detection section 330 calculates chroma from a pixel value of the selected pixel (S102). For example, assuming that among an R component, a G component, and a B component of the pixel value, the largest value is represented by max and the smallest value is represented by min, the chroma S can be calculated by a formula: S=(max−min)/max.

Next, the blur correction non-required region detection section 330 compares the calculated chroma and a chroma threshold value (S103). When the chroma is lower than the chroma threshold value (Yes in S103), the blur correction non-required region detection section 330 detects the selected pixel as the blur correction non-required region (S104). On the contrary, when the chroma is equal to or higher than the chroma threshold value, the blur correction non-required region detection section 330 determines that the selected pixel does not belong to the blur correction non-required region. As understood from the steps S103 and S104, the achromatic color according to the present embodiment does not mean only "chroma S=0", but includes a color having the chroma equal to or lower than the predetermined threshold value.

Next, the blur correction non-required region detection section 330 determines whether the processes in the steps S101 to S104 described above have been performed on all pixels (S105). When any unprocessed pixel remains (No in S105), the blur correction non-required region detection section 330 returns to the step S101 to perform the processes described above on the remaining pixel. When all the pixels have been processed (Yes in S105), the blur correction non-required region detection section 330 terminates the blur correction non-required region detection process.

Alternatively, the hood 1 may be made of plastic. The plastic hood 1 may be transparent (translucent). In such a case, the blur correction non-required region may not be appropriately detected by the determination of whether the hood 1 is achromatic.

Therefore, the blur correction non-required region detection section 330 may detect the blur correction non-required region based on a comparing process with a color of a pixel in a central region of the object image. With a transparent hood, the object such as the tissue on a side deeper than the hood 1 (on a farther side from the imaging section 200) in the region where the hood 1 appears in the object image is observed in a translucent state through the hood 1. Accordingly, although a true color component of the tissue still remains in the pixel in the region where the hood 1 appears, color tones differ from the ones not through the hood 1.

Therefore, assuming that a color of a pixel in a region (central region of the object image) where the hood 1 is quite less likely to appear is set as a reference color, it is presumed that a color of a pixel in the region where the hood 1 appears largely deviates from the reference color. For example, the blur correction non-required region detection section 330 finds an average color of a center of a screen, and detects a pixel whose color deviates from the average color by a predetermined threshold value or more in a color space as the blur correction non-required region. Note that various kinds of color spaces can be used as the color space described herein. For example, when an uniform color space is used as the color space, distance in the color space corresponds to how much the color deviates (color difference), and thus the blur correction non-required region detection section 330 can detect the blur correction non-required region by the comparing process between the distance in the color space and a given threshold value.

3.2 Detection by Time Change in Pixel Value

As described above with reference to FIGS. 3 and 4, the region where the hood 1 appears does not change in position in the object image except for a specific case where the hood 1 is in contact with the tissue (20 and 21), or the like. Accordingly, a change in pixel value in the blur correction non-required region that should be considered is caused only by noise, and thus a change amount is quite small.

Therefore, the blur correction non-required region detection section 330 may detect the blur correction non-required region based on a time change in pixel value in the object image. Specifically, the blur correction non-required region detection section 330 detects a region where the time change in pixel value in the object image is smaller than a predetermined threshold value as the blur correction non-required region.

Figure 8:
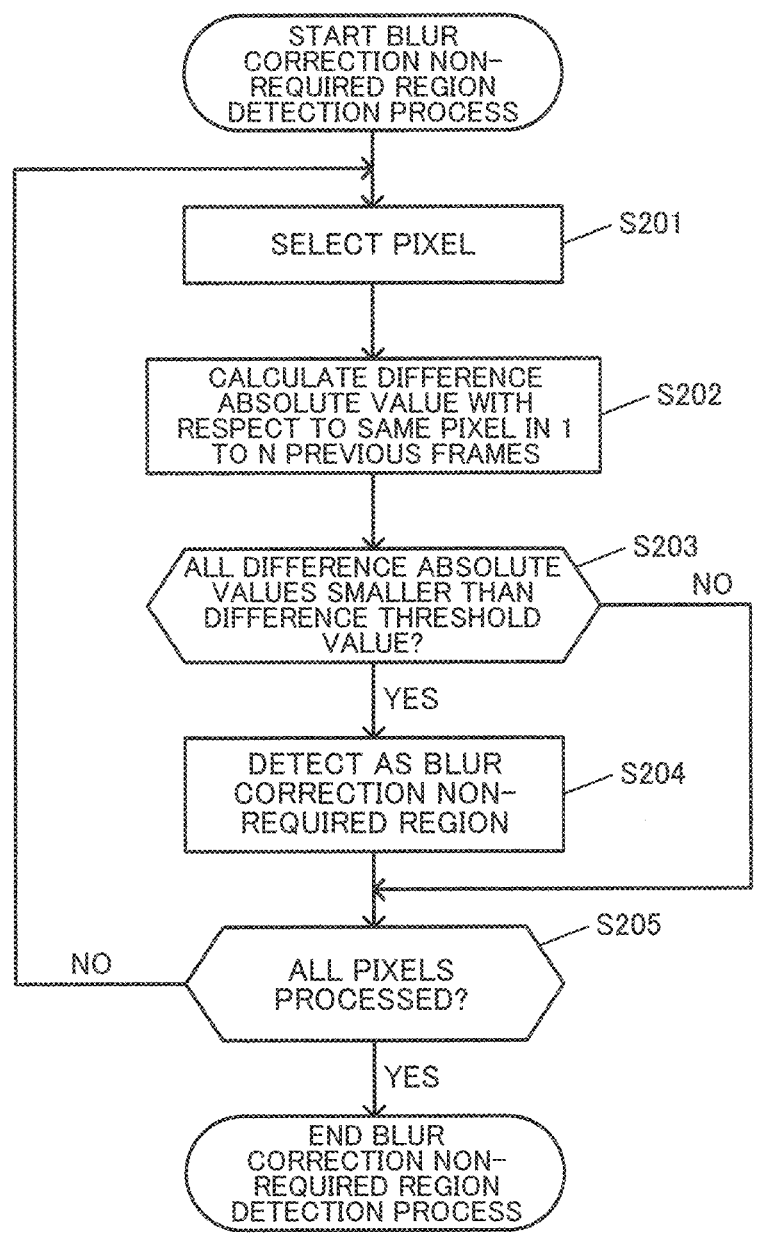
FIG. 8 is a flowchart illustrating a blur correction non-required region detection process.

FIG. 8 is a flowchart illustrating the blur correction non-required region detection process based on the time change in pixel value. When the process starts, the blur correction non-required region detection section 330 selects a pixel serving as a processing target from the object image (S201). Then, the blur correction non-required region detection section 330 calculates a difference absolute value between the pixel value of the selected pixel and a pixel value of the same pixel in a previous frame. There are N (N is an integer of 1 or larger) previous frames, and the blur correction non-required region detection section 330 calculates N difference absolute values (S202). Note that a value of N can be implemented in various modified manners.

Next, the blur correction non-required region detection section 330 compares the calculated difference absolute value and a difference threshold value (S203). When the difference absolute value is smaller than the difference threshold value, the blur correction non-required region detection section 330 detects the pixel as the blur correction non-required region (S204). For example, when all the N difference absolute values calculated in the step S202 are smaller than the difference threshold value, the pixel in question is detected as the blur correction non-required region. Since the change amount of the pixel value is mostly due to the noise, setting the difference threshold value depending on a noise amount enables an appropriate detection process.

Next, the blur correction non-required region detection section 330 determines whether the processes in the steps S201 to S204 described above have been performed on all the pixels (S205). When any unprocessed pixel remains (No in S205), the blur correction non-required region detection section 330 returns to the step S201 to perform the processes described above on the remaining pixel. When all the pixels have been processed (Yes in S205), the blur correction non-required region detection section 330 terminates the blur correction non-required region detection process.

3.3 Pre-Process Based on Position in Object Image

When the hood 1 in a tubular shape is attached to the distal end of the endoscope (distal end of the insertion section 100) as illustrated in FIG. 1, the hood 1 is disposed in a peripheral part (i.e., a region around a central part in the object image, or an edge) in the object image as illustrated by the region A1 in FIG. 2. That is, the blur correction non-required region is disposed in the peripheral part of the object image. In other words, the observation field of vision is a circular region in the central part of the object image, and thus the hood 1 is quite less likely to appear in this region.

Accordingly, the blur correction non-required region detection section 330 may set a region excluding the circular region in the center from the entire object image as a blur correction non-required region detection range, and may perform the blur correction non-required region detection process, described above with reference to FIGS. 7 and 8, with the blur correction non-required region detection range as a target. In this manner, it is possible to avoid erroneously detecting the region (observation field of vision) where the tissue is imaged as the blur correction non-required region. In addition, since the pixels to be processed in the steps S101 to S104 in FIG. 7 and the steps S201 to S204 in FIG. 8 are limited to the pixels in part of the object image, a calculation amount can be reduced.

3.4. Update of Blur Correction Non-Required Region

As described above, a change in position of the blur correction non-required region is small in time series. Accordingly, the blur correction non-required region detection section 330 does not have to frequently (in every frame in a narrow sense) perform the blur correction non-required region detection process, but may use the blur correction non-required region detected at given timing continuously at subsequent timing.

However, when the region of the hood 1 in the image changes, such as when the hood 1 comes into contact with the tissue, the blur correction non-required region needs to be updated in accordance with the change. Without the update, the region where the hood 1 appears and the blur correction non-required region would fail to correspond. As a result, part of the region where the hood 1 appears becomes a target of the blur correction while remaining part does not, which causes an unnatural image where part of the hood 1 slightly moves to be displayed.

Therefore, the blur correction non-required region detection section 330 stops the detection process after detecting the blur correction non-required region until a specific requirement is satisfied, and performs the blur correction non-required region detection process again when the specific requirement is satisfied. Specifically, the blur correction non-required region detection section 330 updates the blur correction non-required region when a time change in pixel value is detected in the blur correction non-required region.

In this manner, the blur correction non-required region can be updated only when the blur correction non-required region needs to be updated. As a result, it is possible to reduce a load for detecting the blur correction non-required region and to appropriately detect (update) the blur correction non-required region in accordance with a situation.

Figure 9:
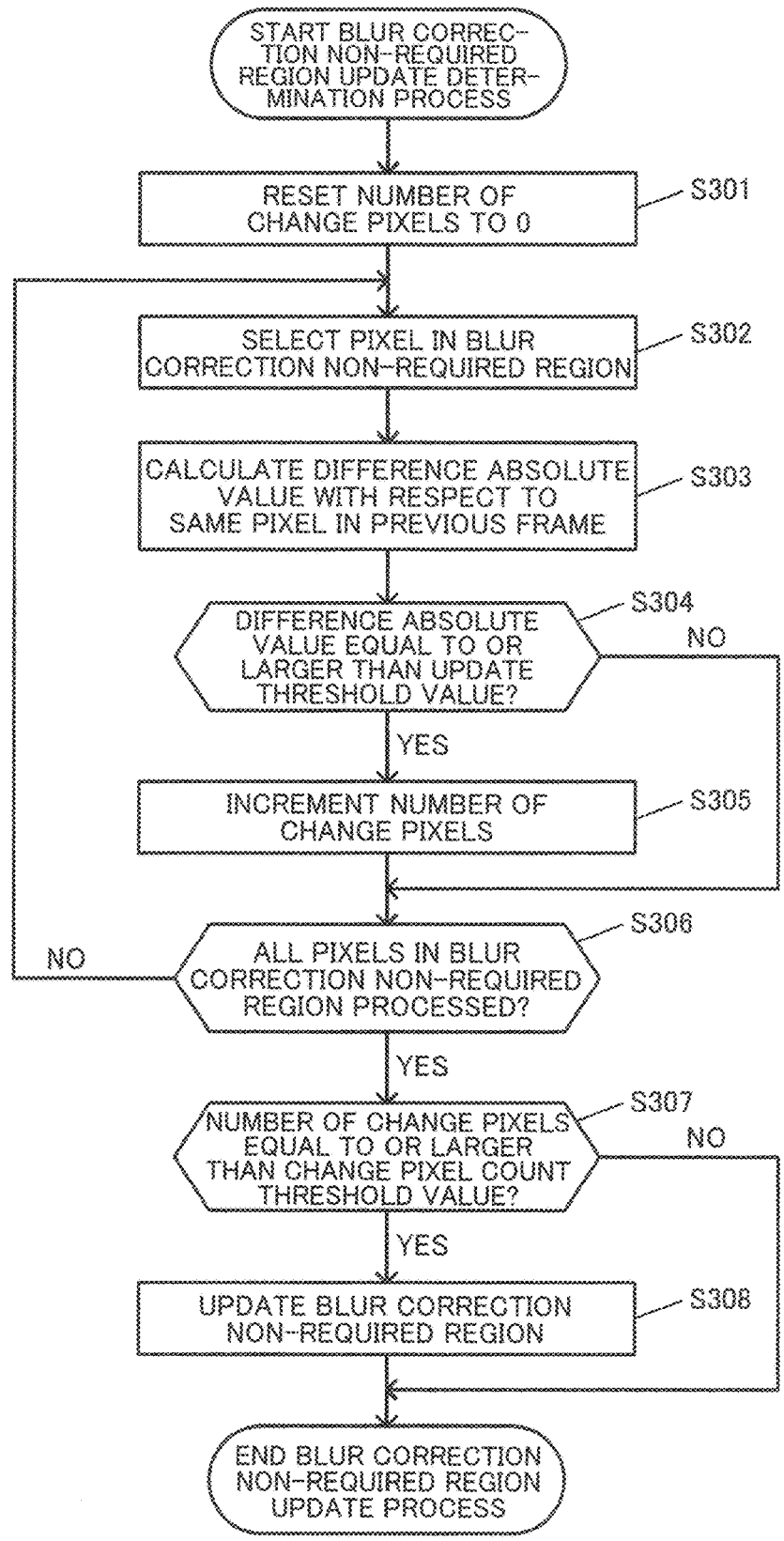
FIG. 9 is a flowchart illustrating a blur correction non-required region update process.

FIG. 9 is a flowchart illustrating a blur correction non-required region update process. When the process starts, the blur correction non-required region detection section 330 resets the number of change pixels to 0 (S301). Next, the blur correction non-required region detection section 330 selects any one of pixels included in the blur correction non-required region (S302). Next, the blur correction non-required region detection section 330 calculates a difference absolute value between the pixel value of the selected pixel and a pixel value of the same pixel in a previous frame (S303). A process in the step S303 may be performed to calculate one difference absolute value with respect to a pixel value in an immediately preceding frame, for example. Alternatively, a plurality of difference absolute values may be calculated using a plurality of previous frames.

Next, the blur correction non-required region detection section 330 compares the calculated difference absolute value and an update threshold value (S304). When the difference absolute value is equal to or larger than the update threshold value (Yes in S304), the blur correction non-required region detection section 330 increments the number of change pixels (S305). When the difference absolute value is smaller than the update threshold value (No in S304), the blur correction non-required region detection section 330 maintains the current number of the change pixels.

Next, the blur correction non-required region detection section 330 determines whether the processes in the steps S301 to S305 described above have been performed on all the pixels in the blur correction non-required region (S306). When any unprocessed pixel remains (No in S306), the blur correction non-required region detection section 330 returns to the step S302 to perform the processes described above on the remaining pixel in the blur correction non-required region.

When all the pixels in the blur correction non-required region have been processed (Yes in S306), the blur correction non-required region detection section 330 compares the number of change pixels and a change pixel count threshold value (S307). When the number of change pixels is equal to or larger than the change pixel count threshold value (Yes in S307), the blur correction non-required region detection section 330 updates the blur correction non-required region (S308). When the number of change pixels is smaller than the change pixel count threshold value (No in S307), the blur correction non-required region detection section 330 determines that updating the blur correction non-required region is not needed.

4. Details of Blur Correction Processing Section

The blur correction processing section 370 performs processes including the blur correction process for finding the blur-corrected region, a processing process in relation to the blank region, and a combining process for combining the blur-corrected region and the blur correction non-required region. Each of the processes is described in detail hereinafter.

4.1 Blur Correction

As illustrated in FIG. 5, the blur correction according to the present embodiment only needs to be performed on the region excluding the blur correction non-required region (i.e., the blur correction target region) and does not need to be performed on the blur correction non-required region.

Accordingly, the blur correction processing section 370 (blur correction section 340) finds the blur-corrected region by a process (first process) in which the blur correction target region is found from the object image based on the blur correction non-required region, and the blur correction is performed on the blur correction target region. The blur correction processing section 370 extracts the region excluding the blur correction non-required region from the object image as the blur correction target region.

Figure 10:
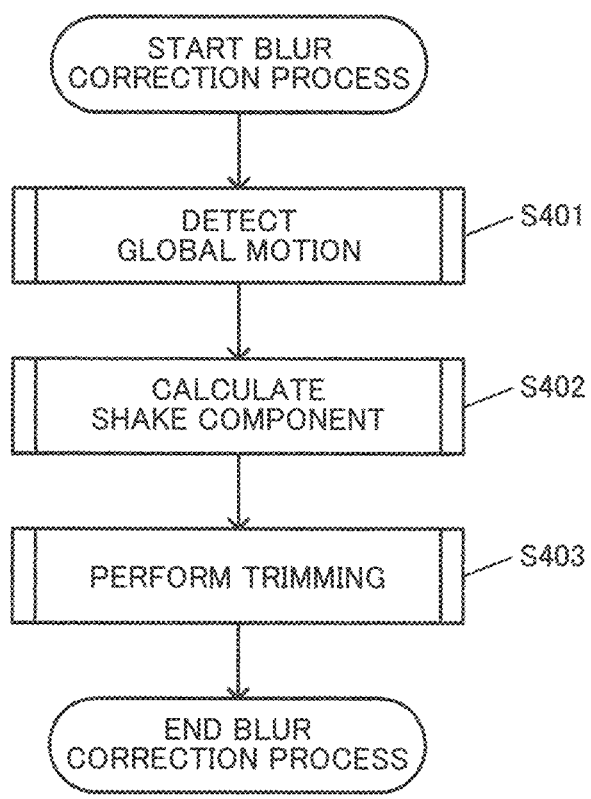
FIG. 10 is a flowchart illustrating a blur correction process.

FIG. 10 is a flowchart illustrating the blur correction process. When the process starts, the blur correction processing section 370 detects global motion information $MV_0$ that represents a global motion of the object in the blur correction target region (S401). The global motion information is, for example, information found with the entire blur correction target region as a target. Accordingly, compared with a case where the blur correction target region is divided into a plurality of local regions and motion information (local motion information) is found for each of the plurality of local regions, the global motion information represents an overall motion of the object.

The motion described herein may be triaxial translation of the imaging section 200. Three axes include, for example, one axis in an optical axis direction, and two axes intersecting (orthogonally in a narrow sense) with the optical axis. That is, the blur correction processing section 370 performs the blur correction with respect to the triaxial translation of the imaging section 200, and uses a parallel component and an orthogonal component to the screen as the global motion information. In this manner, it is possible to perform the blur correction that prevents a change in position of the object in a plane direction (vertical direction or lateral direction) in the image, and a change in size (scaling) of the object in the image.

For example, the blur correction processing section 370 detects a corresponding point by a known method of a scale invariant feature transform (SIFT) from the blur correction target region in a previous frame, and detects the global motion information $MV_0$ based on a correspondence relationship of coordinates of the corresponding point. The global motion information $MV_0$ includes three components including a parallel motion $MVh_0$ in a horizontal direction, a parallel motion $MVv_0$ in a vertical direction, and a change in magnification $MVz_0$ caused by a motion in a depth direction. The blur correction processing section 370 may find the global motion information $MV_0$ by block matching with the blur correction target region as one block. Alternatively, the blur correction processing section 370 may find the global motion information $MV_0$ by dividing the blur correction target region into a plurality of local regions, finding the local motion information by the SIFT or block matching for each of the plurality of local regions, and averaging a plurality of pieces of local motion information.

The global motion information $MV_0$ found in the step S401 includes a motion not caused by the shake of the imaging section 200. Thus, the blur correction processing section 370 calculates a blur correction component (i.e., extracts a shake component S) from the global motion information $MV_0$ (S402). Specifically, the blur correction processing section 370 calculates a motion other than the shake component from previously detected global motions $MV_{M-1}$ to $MV_1$, and subtracts it from the global motion information $MV_0$ to calculate the shake component S. The global motion information $MV_i$ (i is an integer of 1 or larger and M−1 or smaller and M is a given integer of 2 or larger) described herein represents the global motion information calculated i frames earlier. For example, the blur correction processing section 370 calculates a motion $MV_{mean}$ other than the shake by a formula (1) below and the shake component S by a formula (2) below. In other words, the shake component S is calculated assuming that the global motion information $MV_0$ is a result of superimposition of the motion (S) by a sudden shake on a mean motion ($MV_{mean}$).

[Formula 1]

$$MV_{mean} = \frac{\sum_{i=0}^{M-1} MV_i}{M} \quad (1)$$

$$S = MV_0 - MV_{mean} \quad (2)$$

Similarly to the global motion information $MV_0$, the shake component S described herein includes three components including a parallel motion Sh in a horizontal direction, a parallel motion Sv in a vertical direction, and a change in magnification Sz caused by a motion in a depth direction.

Next, the blur correction processing section 370 trims the blur correction target region in such a manner as to cancel the calculated shake component S so as to find the blur-corrected region (S403). Specifically, when the respective components of the shake component S are Sh pixels, Sv pixels, and Sz magnifications, the blur correction processing section 370 trims the blur correction target region by −Sh pixels in the horizontal direction and by −Sv pixels in the vertical direction, and then magnifies the resultant region by 1/Sz times. In order to interpolate a pixel value, a known bicubic interpolation method is used, for example. However, the interpolation method of the pixel value is not limited to this.

In this manner, the blur correction can be performed only on the blur correction target region.

However, a specific procedure is not limited to the one described above as long as the blur-corrected region is found in the present embodiment. For example, it is possible to find the blur-corrected region without directly finding the blur correction target region.

Specifically, the blur correction processing section 370 (blur correction section 340) may find the blur-corrected region by a process (second process) in which a blur-corrected image is found by performing the blur correction on the object image, and the blur correction is cancelled in a region corresponding to the blur correction non-required region in the blur-corrected image. Also this process makes it possible to find the blur-corrected region, that is, perform the blur correction on the region excluding the blur correction non-required region (i.e., the blur correction target region) without performing the blur correction on the blur correction non-required region.

4.2 Processing of Blank Region

As described above, the blur-corrected region is a region where the parallel motion and the scaling are performed on the blur correction target region (or a region corresponding to that region).

Figure 11:
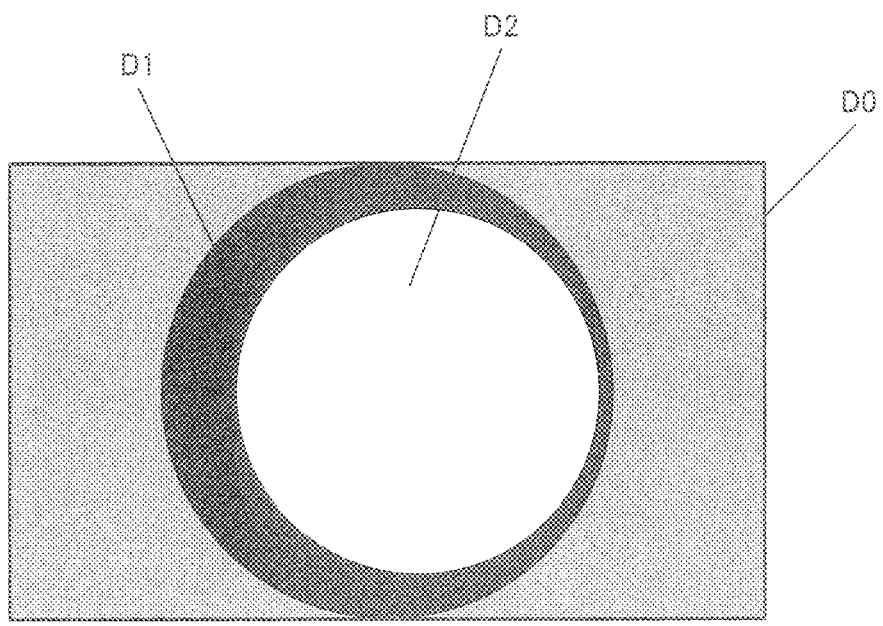
FIG. 11 is a diagram illustrating a method for padding a blank region.

FIG. 11 illustrates an example of a relationship between the blur-corrected region found by the blur correction process and the blur correction target region. In the example in FIG. 11, the blur correction target region (D1) in a circular shape is moved in a right direction and reduced in size so as to consequently find the blur-corrected region (D2). An image D0 represents a whole object image. As illustrated in FIG. 11, a pixel in the blur correction target region may not be included in the blur-corrected region due to the blur correction, and thus a pixel value of the pixel in question (blank region D1∩¬D2) becomes indefinite.

Accordingly, the blur correction processing section 370 (blur correction section 340) detects the blank region that does not belong to either the blur-corrected region or the blur correction non-required region. Then, the blur correction processing section 370 performs the processing process on the detected blank region. In this manner, the pixel value in the blank region can be appropriately determined even if the blank region is generated.

For example, the blur correction processing section 370 pads a region including the blank region with a specific signal value. As illustrated in the example in FIG. 11, the blank region may be padded with black (pixel value=0). In this manner, display can be stabilized.

Alternatively, the blur correction processing section 370 may interpolate the blank region from the object image previously obtained. In the present embodiment, the global motion information ($MV_{M-1}$ to $MV_1$) has been found with respect to the image in the previous frame. By using the global motion information, a positional relationship between the object imaged in the blur correction target region in the current frame and the object imaged in the previous frame can be specified. Accordingly, when the object at a position corresponding to the blank region in the current frame has been imaged in the previous frame, the object may be displayed in the blank region of the current frame. At this time, magnification, reduction, rotation, or the like may be performed as necessary. By the interpolation using the previous frame, the object such as the tissue can also be displayed in the blank region. That is, an area of the blank region can be reduced.

However, in the method described above, the region where the desired object (tissue) is displayed may change in position, size, and shape in each frame, which makes the image hard to see for the user.

Accordingly, the blur correction processing section 370 may pad part of the blur-corrected region with a specific signal value such that the region including the blank region is formed into a predetermined shape. The predetermined shape described herein is a ring shape including a region surrounded by two circles (concentric circles in a narrow sense), for example.

Figure 12A:
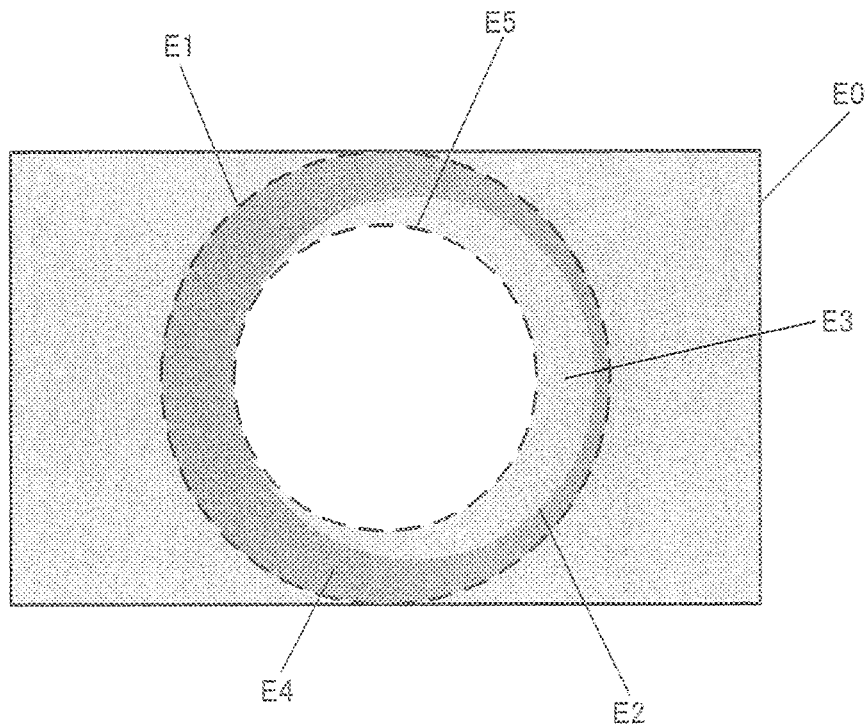
FIG. 12A and FIG. 12B are diagrams illustrating a method for forming a region including the blank region into a predetermined shape.
Figure 12B:
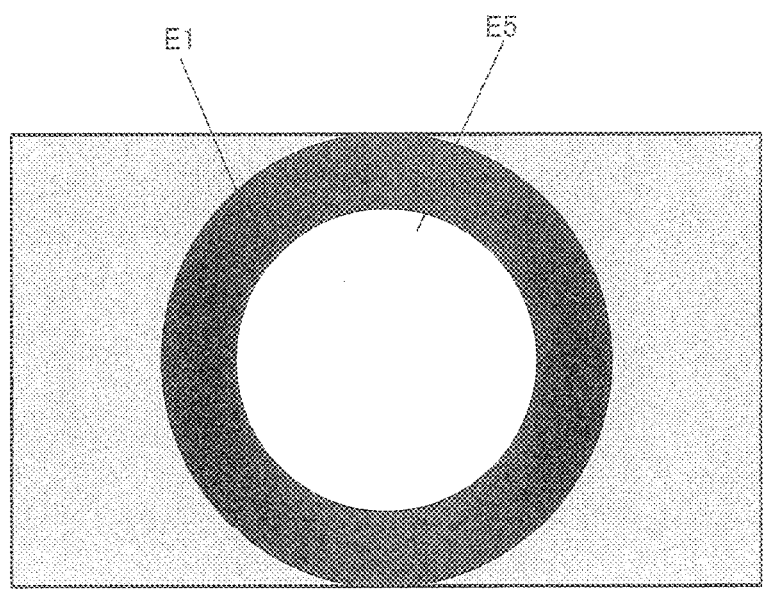

FIGS. 12A and 12B illustrate an example of processing of the blur-corrected region. The whole object image (E0), the blur correction target region (E1), and the unprocessed blur-corrected region (E2) are the same as those in FIG. 11, and the regions E1 and E2 are circular. The blur correction processing section 370 pads a region E3 in the blur-corrected region E2 with the predetermined signal value (e.g., black, pixel value=0). In this manner, a region (E4∪E3) including an originally blank region (E4, which is the same as the blank region in FIG. 11) and the padded blur-corrected region (E3) becomes a ring shape. The ring shape described herein is a shape between a first circle (boundary of a region E5 in FIG. 12A) and a second circle (boundary of the blur correction target region E1 in FIG. 12A) that is larger than the first circle and concentric with the first circle.

The process described above can be considered as a process in which the ring shape including the entire blank region is set, and a pixel in the region (E3) in the blur-corrected region (E2) included in the ring shape is treated as the blank region. In this manner, a change in shape of the region where the desired object is displayed (i.e., a change in shape of the blank region) does not occur, thereby reducing stress in observation. An example of a display image in this case is illustrated in FIG. 12B. In the example in FIG. 12B, the region to be padded with the specific signal value always becomes the ring shape, and an observation region (processed blur-corrected region, E5=E2∩¬E3) always becomes a circular shape with a center of the object image as its center.

In the method in FIGS. 12A and 12B, since part of the blur-corrected region is padded with the specific signal value, part of information about the imaged object is lost. However, a degree of the blur correction (i.e., a degree of reduction of the shake by the blur correction) has an upper limit. Accordingly, a degree of the motion and the change in shape of the blur-corrected region relative to the original blur correction target region also has an upper limit, and thus an upper limit of the information to be lost can be presumed. In order to comprehensively show the region, the degree of the motion and the change in shape of the blur-corrected region is emphasized in FIGS. 12A and 12B, however, an area of the region (E3) whose information is actually lost may be considered so small that it cannot cause any problem.

Alternatively, the blur correction processing section 370 (blur correction section 340) may previously magnify the blur correction target region to avoid generating the blank region.

Figure 13:
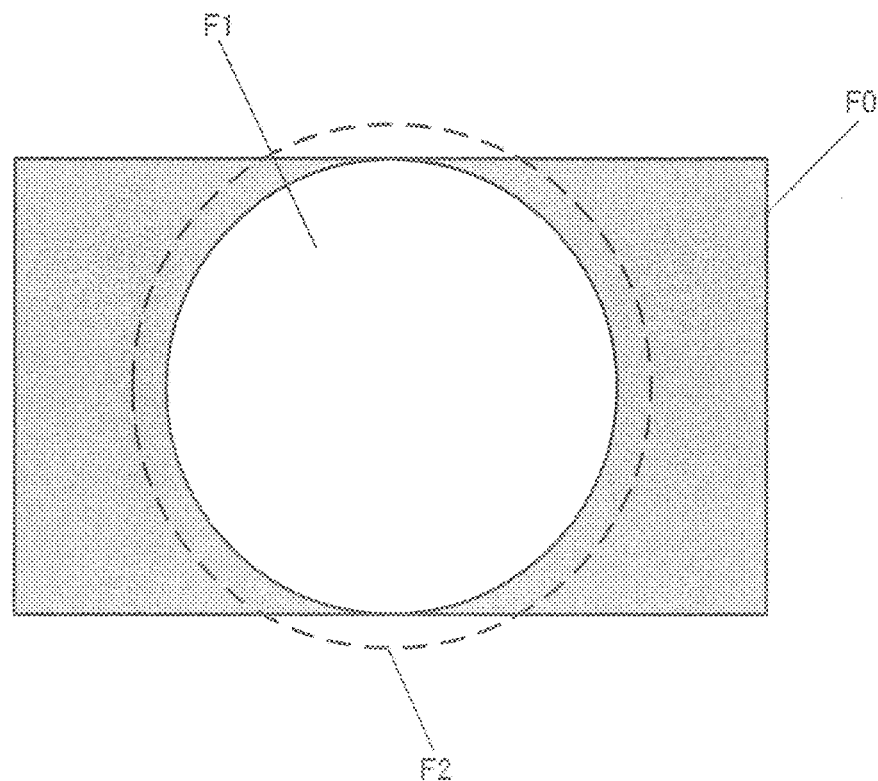
FIG. 13 is a diagram illustrating a method for magnifying a blur correction target region.

FIG. 13 is an image example when the blur correction target region is magnified. In FIG. 13, an image F0 represents a whole object image, a region F1 represents the blur correction target region before it is magnified, and a region F2 represents the blur correction target region after it is magnified. As illustrated by the region F2, previously magnifying the blur correction target region can provide the region with a margin in the number of pixels, compared with an original blur correction target region. For example, assuming that the shake occurs only in the optical axis direction, the blur correction to be performed is scaling of the blur correction target region by $1/S_z$ times. Thus, assuming that the largest value of $S_z$ to be presumed is $S_{zmax}$, previously magnifying the blur correction target region by $S_{zmax}$ times can prevent generation of the blank region. In addition, assuming that the shake occurs only in the plane direction, the blur correction to be performed is moving (trimming) the blur correction target region in the horizontal direction by $-S_h$ pixels and in the vertical direction by $-S_v$ pixels. Accordingly, it is possible to prevent the generation of the blank region by previously magnifying the blur correction target region such that the numbers of pixels in the horizontal and vertical directions in a marginal region generated due to the magnification become the presumed largest values of $S_h$ and $S_v$. The shake naturally occurs in both the optical axis direction and the plane direction. Thus, a magnification ratio of the blur correction target region may be set considering both the parallel motion and the scaling.

FIG. 13 illustrates the example in which the blur correction target region is magnified before the blur correction, however, a region on which the blur correction has been performed (i.e., the blur-corrected region) may be magnified. Alternatively, although the observation field of vision in the output image becomes smaller, the generation of the blank region can be prevented by magnifying the blur correction non-required region. The blur correction processing section 370 magnifies at least one of the blur correction target region, the blur-corrected region, and the blur correction non-required region such that the blank region disappears by the combination of the blur-corrected region and the blur correction non-required region. The blur correction processing section 370 may magnify any one of or two or more of the blur correction target region, the blur-corrected region, and the blur correction non-required region.

In this manner, the blank region can be eliminated from the display, thereby reducing stress in observation.

In addition, a blur correction amount representing a degree of the blur correction is information that has been known as a setting value of the blur correction. The blur correction amount described herein is information for defining the largest values of a motion amount and a change amount in shape of the object in the image that are subject to the blur correction. For example, it is information representing the largest values of $S_h$, $S_v$, and $S_z$ described above or information for finding the largest values of $S_h$, $S_v$, and $S_z$.

The blur correction processing section 370 may magnify at least one of the blur correction target region, the blur-corrected region, and the blur correction non-required region based on the blur correction amount representing the degree of the blur correction. That is, using the blur correction amount enables a magnification process in which no blank region is generated from the beginning, and thus the blur correction processing section 370 does not need to detect the blank region.

4.3 Image Combination

As described above, in the processes of the present embodiment, two regions including the blur-corrected region (processed blur-corrected region according to circumstances) and the blur correction non-required region are found, and the positional relationship between the two regions changes depending on a state of the shake. Accordingly, the display image processing section 370 (image combining section 350) needs to perform a process for combining the blur-corrected region and the blur correction non-required region to generate the display image.

Figure 14:
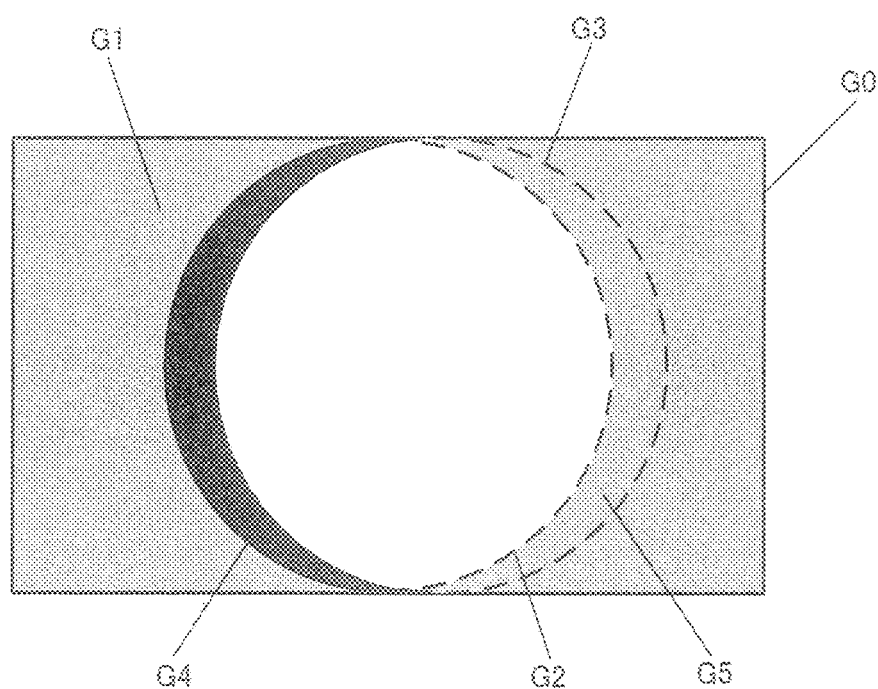
FIG. 14 is a diagram illustrating a combining process for combining the blur correction non-required region and a blur-corrected region.

FIG. 14 is a diagram illustrating a method for image combination of the blur-corrected region and the blur correction non-required region. In FIG. 14, an image G0 represents a whole object image, a region G1 represents the blur correction non-required region, a circular region G2 represents the blur correction target region, and a circular region G3 represents the blur-corrected region. A region G4 is a region (G2∩¬G3) that belongs to the blur correction target region but does not belong to the blur-corrected region, and represents the blank region. A region G5 is a region (G1∩G3) that belongs to both the blur-corrected region and the blur correction non-required region.

In a region (G1∩¬G3) that belongs to the blur correction non-required region but does not belong to the blur-corrected region, only one pixel value originated from the blur correction non-required region is obtained, and thus the pixel value in the blur correction non-required region is used. On the contrary, in the region G5, both a pixel value in the blur correction non-required region and a pixel value in the blur-corrected region exist. The method according to the present embodiment is for preventing the blur correction non-required region from being changed (moved) by the blur correction. Accordingly, the image combining section 350 uses the pixel value in the blur correction non-required region also for the region G5 that belongs to both the blur-corrected region and the blur correction non-required region. In this manner, as for the pixel that originally belongs to the blur correction non-required region (G1), the image combining section 350 maintains the pixel value in the blur correction non-required region regardless of whether the pixel belongs to the blur-corrected region (G3).

As for the region (G2∩G3) that belongs to both the blur correction target region and the blur-corrected region, the image combining section 350 displays the pixel value in the blur-corrected region. In this manner, a result of performing the blur correction on the blur correction target region can be displayed. As for the blank region (G4), various processing described above is possible. In the example in FIG. 14, the pixel value=0. In this manner, the blur-corrected region and the blur correction non-required region can be appropriately combined to generate the display image.

In accordance with one of some embodiments, there is provided a blur correction device comprising a processor including hardware, the processor being configured to implement:

obtaining an object image from an imaging section that forms an image of reflected light from an object;

setting any one of a first region where a blur correction is not applied and a second region where the blur correction is applied, based on the object image;

finding a third region representing a result of the blur correction applied to the second region; and combining the third region and the first region.

In accordance with one of some embodiments, there is provided an endoscope apparatus comprising:

the blur correction device;

an insertion section configured to be inserted into a body;

a hood configured to be attached to a distal end of the insertion section; and an image sensor configured to be connected to the insertion section.

In accordance with one of some embodiments, there is provided a blur correction method comprising:

obtaining an object image from an imaging section that forms an image of reflected light from an object;

setting any one of a first region where a blur correction is not applied and a second region where the blur correction is applied, based on the object image;

finding a third region representing a result of the blur correction applied to the second region; and combining the third region and the first region.

In accordance with one of some embodiments, there is provided a blur correction device comprising:

an image acquisition section configured to obtain an object image from an imaging section configured to form an image of reflected light from an object;

a region detection section configured to detect a first region where a blur correction is not applied based on the object image; and a blur correction processing section configured to find a third region representing a result of the blur correction applied to a second region, and to combine the third region thus found and the first region, the second region being a region excluding the first region from the object image.

Although the embodiments and the modifications have been described in detail above, the present disclosure is not limited to the embodiments and the modifications as they are, and various modifications and variations in components may be made in implementation without departing from the scope of the present disclosure. A plurality of elements disclosed in the embodiments and the modifications may be combined as appropriate. For example, some of all the elements described in the embodiments and the modifications may be deleted. Furthermore, elements in different embodiments and modifications may be combined as appropriate. Any term cited with a different term having a broader meaning or the same meaning at least once in the specification and the drawings can be replaced by the different term in any place in the specification and the drawings. Thus, various modifications and applications can be made without departing from the scope of the present disclosure.

What is claimed is:

1. A blur correction device comprising a processor including hardware, the processor being configured to implement:

obtaining an object image from an imaging section that forms an image of reflected light from an object;

setting any one of a first region where a blur correction is not applied and a second region where the blur correction is applied, based on the object image;

finding a third region representing a result of the blur correction applied to the second region; and combining the third region and the first region.

2. The blur correction device as defined in claim 1, wherein the processor implements finding the third region by any one of a first process in which the second region is found from the object image based on the first region and the blur correction is performed on the second region, and a second process in which the blur correction is performed on the object image to find a blur-corrected image and the blur correction is cancelled in a region corresponding to the first region in the blur-corrected image.

3. The blur correction device as defined in claim 1, wherein
the processor implements
detecting a fourth region that belongs to neither the third region nor the first region.

4. The blur correction device as defined in claim 3, wherein
the processor implements
interpolating the fourth region from the object image previously obtained.

5. The blur correction device as defined in claim 3, wherein
the processor implements
padding a region including the fourth region with a specific signal value.

6. The blur correction device as defined in claim 5, wherein
the processor implements
padding part of the third region with the specific signal value such that the region including the fourth region is formed into a predetermined shape.

7. The blur correction device as defined in claim 3, wherein
the processor implements
magnifying at least one of the second region, the third region, and the first region such that the fourth region disappears by the combination of the third region and the first region.

8. The blur correction device as defined in claim 1, wherein
the processor implements
magnifying at least one of the second region, the third region, and the first region based on a blur correction amount representing a degree of the blur correction.

9. The blur correction device as defined in claim 1, wherein
the processor implements
detecting the first region based on a color of a pixel in the object image.

10. The blur correction device as defined in claim 9, wherein
the processor implements
detecting a region where the color of the pixel in the object image is achromatic as the first region.

11. The blur correction device as defined in claim 9, wherein
the processor implements
detecting the first region based on a comparing process with a color of a pixel in a central region of the object image.

12. The blur correction device as defined in claim 1, wherein
the processor implements
detecting the first region based on a time change in pixel value of the object image.

13. The blur correction device as defined in claim 12, wherein
the processor implements
detecting a region where the time change in pixel value of the object image is smaller than a predetermined threshold value as the first region.

14. The blur correction device as defined in claim 1, wherein
the processor implements
updating the first region when a time change in pixel value is detected in the first region.

15. The blur correction device as defined in claim 1, wherein
the first region is disposed in a peripheral part of the object image.

16. The blur correction device as defined in claim 1, wherein
the processor implements
performing the blur correction with respect to triaxial translation of the imaging section.

17. An endoscope apparatus comprising:
the blur correction device as defined in claim 1;
an insertion section configured to be inserted into a body;
a hood configured to be attached to a distal end of the insertion section; and
an image sensor configured to be connected to the insertion section.

18. A blur correction method comprising:
obtaining an object image from an imaging section that forms an image of reflected light from an object;
setting any one of a first region where a blur correction is not applied and a second region where the blur correction is applied, based on the object image;
finding a third region representing a result of the blur correction applied to the second region; and
combining the third region and the first region.

19. A blur correction device comprising:
an image acquisition section configured to obtain an object image from an imaging section configured to form an image of reflected light from an object;
a region detection section configured to detect a first region where a blur correction is not applied based on the object image; and
a blur correction processing section configured to find a third region representing a result of the blur correction applied to a second region, and to combine the third region and the first region, the second region being a region excluding the first region from the object image.

* * * * *